US011903652B2

(12) United States Patent
Couture et al.

(10) Patent No.: US 11,903,652 B2
(45) Date of Patent: Feb. 20, 2024

(54) SURGERY ASSISTANCE SYSTEM

(71) Applicant: ORTHOSOFT ULC, Montreal (CA)

(72) Inventors: Pierre Couture, Montreal (CA);
Ramnada Chav, Laval (CA);
Sebastien Parratte, Marseilles (FR);
Kevin Unger, Montreal (CA)

(73) Assignee: ORTHOSOFT ULC, Montreal (CA)

( * ) Notice: Subject to any disclaimer, the term of this patent is extended or adjusted under 35 U.S.C. 154(b) by 462 days.

(21) Appl. No.: 17/085,345

(22) Filed: Oct. 30, 2020

(65) Prior Publication Data

US 2021/0128244 A1 May 6, 2021

Related U.S. Application Data

(60) Provisional application No. 62/927,815, filed on Oct. 30, 2019.

(51) Int. Cl.
*A61B 34/10* (2016.01)
*A61B 34/37* (2016.01)
(Continued)

(52) U.S. Cl.
CPC .............. *A61B 34/10* (2016.02); *A61B 34/20* (2016.02); *A61B 34/37* (2016.02); *G06N 20/00* (2019.01);
(Continued)

(58) Field of Classification Search
CPC ......... A61B 34/10; A61B 34/20; A61B 34/37; A61B 2034/102; A61B 2034/105; G06N 20/00
See application file for complete search history.

(56) References Cited

U.S. PATENT DOCUMENTS 5,499,293 A    3/1996  Behram et al.
8,498,883 B2   7/2013  Lorsch
               (Continued)

FOREIGN PATENT DOCUMENTS

EP     3367387 A1    8/2018
WO     2005072629 A1 8/2005

OTHER PUBLICATIONS

Twinanda, A. P., Yengera, G., Mutter, D., Marescaux, J., & Padoy, N. (2018). RSDNet: Learning to predict remaining surgery duration from laparoscopic videos without manual annotations. IEEE transactions on medical imaging, 38(4), 1069-1078. (Year: 2018).*

(Continued)

*Primary Examiner* — Bijan Mapar
(74) *Attorney, Agent, or Firm* — NORTON ROSE FULBRIGHT CANADA LLP

(57) ABSTRACT

A surgical assistance system includes a processing unit; and a non-transitory computer-readable memory communicatively coupled to the processing unit and comprising computer-readable program instructions executable by the processing unit for: obtaining a video feed of a surgical procedure and monitoring the surgical procedure from the video feed; detecting, from an image processing of the video feed, a condition requiring a deviation from the surgical procedure, the deviation being defined as being outside of a standard surgical flow; and outputting a recommendation of deviation by intra-operatively providing the recommendation to an operator of the surgical procedure.

18 Claims, 8 Drawing Sheets

(51) Int. Cl.
  *G06N 20/00*   (2019.01)
  *A61B 34/20*   (2016.01)
(52) U.S. Cl.
  CPC ... *A61B 2034/102* (2016.02); *A61B 2034/105* (2016.02)

(56) References Cited

U.S. PATENT DOCUMENTS

| | | |
|---|---|---|
| 9,788,907 B1 | 10/2017 | Alvi et al. |
| 10,226,302 B2 | 3/2019 | Lacal et al. |
| 2019/0231433 A1 | 8/2019 | Amanatullah |

OTHER PUBLICATIONS

Vercauteren, T., Unberath, M., Padoy, N., & Navab, N. (2019). Cai4cai: the rise of contextual artificial intelligence in computer-assisted interventions. Proceedings of the IEEE, 108(1), 198-214. (Year: 2019).*

Esfandiari, H., Newell, R., Anglin, C., Street, J., & Hodgson, A. J. (2018). A deep learning framework for segmentation and pose estimation of pedicle screw implants based on C-arm fluoroscopy. International journal of computer assisted radiology and surgery, 13, 1269-1282. (Year: 2018).*

Tan, Tina, "How Verb Surgical Will Deliver On Surgery 4.0", Clinica; https://medtech.pharmaintelligence.informa.com/MT121764/Exec-Chat-How-Verb-Surgical-Will-Deliver-On-Surgery-40, (Nov. 14, 2017), 5 pgs.

* cited by examiner

SURGERY ASSISTANCE SYSTEM

CROSS-REFERENCE TO RELATED APPLICATION

The present application claims the priority of U.S. Patent Application No. 62/927,815, filed on Oct. 30, 2019 and incorporated herein by reference.

TECHNICAL FIELD

The present application relates to computer-assisted surgery, such as computer-assisted surgery systems used in orthopedic surgery to track bones and tools, and to robotic surgery systems.

BACKGROUND OF THE ART

Computer-assisted surgery commonly employs tracker systems to provide an operator with navigation data through a surgical procedure. The navigation data may take various forms, including position and orientation data pertaining to bones and tools, predicted alterations, imaging, etc. The computer-assisted surgery systems may also include robotic apparatuses to perform some steps of surgical procedures.

In such systems, an operating system follows a surgical flow, i.e., a sequence of steps or actions that must be followed according to a predetermined order. However, the surgical flows may not be fully adapted to each patient. Surgical flows may be based on standard parameters for patients, even though human anatomy varies expansively according to numerous factors, including age, gender, race, genetics, congenital conditions, pathologies, to name but a few of such factors.

SUMMARY

In accordance with one aspect of the present disclosure, there is provided a surgical assistance system comprising: a processing unit; and a non-transitory computer-readable memory communicatively coupled to the processing unit and comprising computer-readable program instructions executable by the processing unit for: obtaining a video feed of a surgical procedure and monitoring the surgical procedure; detecting, from the video feed, a condition requiring a deviation from the surgical procedure, the deviation being defined as being outside of a standard surgical flow; and outputting a recommendation of deviation by intra-operatively providing the recommendation to a surgeon operating the robotic surgical device.

According to an aspect, there is provided a surgical assistance system comprising: a processing unit; and a non-transitory computer-readable memory communicatively coupled to the processing unit and comprising computer-readable program instructions executable by the processing unit for: obtaining a video feed of a surgical procedure and monitoring the surgical procedure from the video feed; detecting, from an image processing of the video feed, a condition requiring a deviation from the surgical procedure, the deviation being defined as being outside of a standard surgical flow; and outputting a recommendation of deviation by intra-operatively providing the recommendation to an operator of the surgical procedure.

In some embodiments, the system further comprises a machine learning module and wherein the instructions further cause the processing unit to train the machine learning module using at least a video feed of prior surgical procedures to determine conditions requiring the deviation from the surgical procedure.

In some embodiments, the machine learning module is trained by performing image processing of the video feed of prior surgical procedures.

In some embodiments, the machine learning module is trained by receiving control data associated with the video feed from computer-assisted surgery controllers of the prior surgical procedures.

In some embodiments, the machine learning module is trained by receiving patient data associated with the video feed, the patient data including one or more of age, gender, race, ethnicity, genetics, height, weight, body mass index, congenital conditions, pathologies, medical history.

In some embodiments, the machine learning module is trained by receiving tool data associated with the video feed.

In some embodiments, the machine learning module is trained by receiving post-operative assessment data associated with the prior surgical procedures.

In some embodiments, receiving post-operative assessment data includes receiving quantitative post-operative assessment data.

In some embodiments, receiving post-operative assessment data includes receiving qualitative post-operative assessment data.

In some embodiments, obtaining a video feed of a surgical procedure includes receiving a RGB camera video feed.

In some embodiments, obtaining a video feed of a surgical procedure and monitoring the surgical procedure from the video feed includes receiving the video feed from a tracking apparatus used in the surgical flow.

In some embodiments, the computer-readable program instructions executable by the processing unit are further for receiving control data associated with the video feed of the surgical procedure from a computer-assisted surgery controller of the surgical procedure.

In some embodiments, the computer-readable program instructions executable by the processing unit are further for receiving patient data associated with the video feed of the surgical procedure, the patient data including one or more of age, gender, race, ethnicity, genetics, height, weight, body mass index, congenital conditions, pathologies, medical history.

In some embodiments, outputting a recommendation of deviation includes outputting a recommendation of substitution of at least one step from the standard surgical flow.

In some embodiments, outputting a recommendation of deviation includes outputting a recommendation of at least one additional step before pursuing the standard surgical flow.

In some embodiments, outputting a recommendation of deviation includes outputting a recommendation of cancelling at least one step before pursuing the standard surgical flow.

In some embodiments, outputting a recommendation of deviation includes outputting a recommendation of repeating at least one step before pursuing the standard surgical flow.

In some embodiments, monitoring the surgical procedure from the video feed includes inserting at least one bookmark in the video feed.

In some embodiments, monitoring the surgical procedure from the video feed includes labelling at least one step of the surgical procedure in the video feed.

The surgical assistance system may be provided on a server.

In some embodiments, the surgical assistance system comprises an interface configured to receive the video feed, for example from a camera.

According to an aspect, there is provided a surgical assistance apparatus comprising: an interface for obtaining a video feed of a surgical procedure; a processing unit configured to: monitor the surgical procedure from the video feed; detect, from an image processing of the video feed, a condition requiring a deviation from the surgical procedure, the deviation being defined as being outside of a standard surgical flow; output a recommendation of deviation by intra-operatively providing the recommendation to an operator of the surgical procedure.

According to an aspect, there is provided a surgical assistance method comprising: obtaining a video feed of a surgical procedure and monitoring the surgical procedure from the video feed; detecting, from an image processing of the video feed, a condition requiring a deviation from the surgical procedure, the deviation being defined as being outside of a standard surgical flow; and outputting a recommendation of deviation by intra-operatively providing the recommendation to an operator of the surgical procedure.

In accordance with another aspect of the present disclosure, there is provided a surgical assistance system comprising: a processing unit; and a non-transitory computer-readable memory communicatively coupled to the processing unit and comprising computer-readable program instructions executable by the processing unit for: obtaining tracking data from a first tracking apparatus during surgical procedure; obtaining a video feed of the surgical procedure from a camera separate from the first tracking apparatus; training a machine learning module using at least the video feed and the tracking data to perform tracking; and outputting the machine learning module parametrized to output tracking data with the video feed from the camera and without the tracking data from the first tracking apparatus.

DETAILED DESCRIPTION

Figure 1:
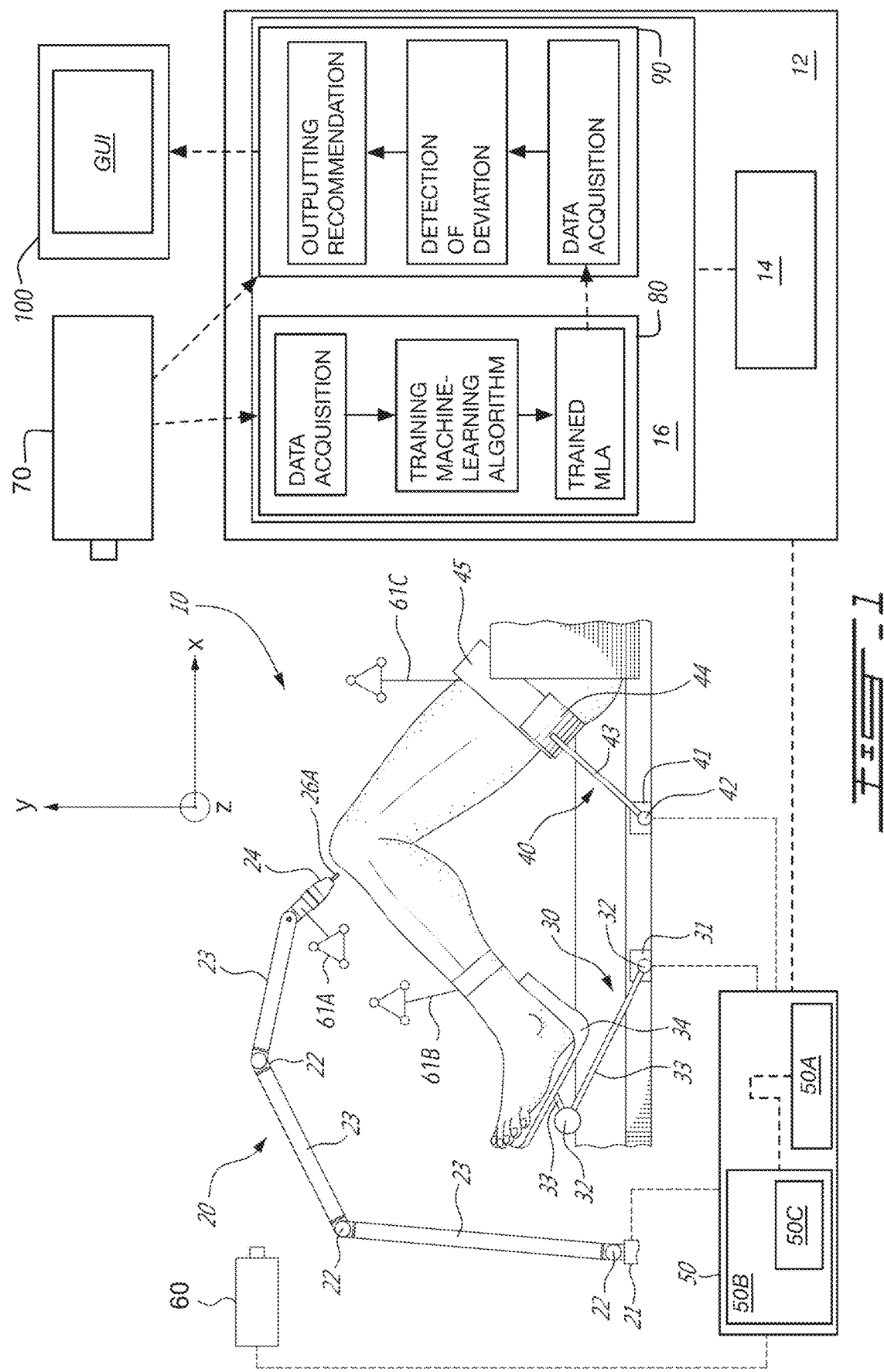
FIG. 1 is a schematic view of a surgery assistance system in accordance with a first embodiment of the present disclosure.

Referring to FIG. 1, a surgery assistance (SA) system in accordance with the present disclosure is generally shown at 10. The SA system 10 may be used to perform at least some of the steps of method 110 of FIG. 2. The SA system 10 is shown relative to a patient's knee joint in supine decubitus, but only as an example. The SA system 10 could be used for other body parts, including non-exhaustively hip joint, spine, and shoulder bones, in orthopedic surgery in which bones are altered to receive implants, or other types of surgery. The SA system 10 may include a server 12 comprising one or more processing units 14, such as conventional central processing unit(s) (CPU(s)), and a non-transitory computer-readable memory 16 communicatively coupled to the one or more processing units 14. The memory 16 may store therein computer-readable instructions. The server 12 may be implemented in any suitable way. For example, in the present embodiment the server 12 is shown as a single entity, which may be a suitable computer for example with the associated communications hardware, input-output hardware, and controls hardware to give a few examples, all of which may be selected, for example from conventional hardware, to suit each particular embodiment of the other components of the SA system 10. In other embodiments, the server 12 may be implemented in a distributed manner, with for example parts thereof being physical parts while other parts may be simulated, such as via virtual machines for example, and/or yet other parts thereof may be remote. The server 12 may also be cloud-based.

The SA system 10 may or may not be robotized. The SA system 10 may operate in parallel with a computer-assisted surgery (CAS) system that may optionally be a robotized surgery system. The CAS system may include a robot arm 20, a foot support 30, a thigh support 40, a CAS controller 50 which may be a robotized surgery controller if a robot arm 20 is used, and/or a tracking apparatus 60. The CAS system may be used independently of machine-learning assistance, but over time, machine-learning assistance may assist and contribute to the surgical flow, in the manner described below. The SA system 10 may include a camera 70, a machine-learning module 80, and an assistance module 90 in the form of computer-readable instructions in the memory 16. One or more devices 100, such as monitors, tablets, phones, and the like, may be operatively connected to the server 12 and may display a graphical-user interface (GUI):

The robot arm 20 is optional and is operatively connected to and is the working end of the SA system 10 in an embodiment featuring robotics, and is used to perform bone alterations as planned by an operator and/or the CAS controller 50 and as controlled by the CAS controller 50.

The foot support 30 is optional and supports the foot and lower leg of the patient, in such a way that it is only selectively movable. The foot support 30 is robotized in that its movements can be controlled by the CAS controller 50. The support 30 could take other forms depending on the nature of the surgery, such as a shoulder surgery.

The thigh support 40 is optional and supports the thigh and upper leg of the patient, again in such a way that it is only selectively or optionally movable. The thigh support 40 may optionally be robotized in that its movements can be controlled by the CAS controller 50. The support 40 could take other forms depending on the nature of the surgery.

The CAS controller 50 operates the surgical workflow and at least part of the method 110. The CAS controller 50 may also control the robot arm 20, the foot support 30, and/or the thigh support 40. The CAS controller 50 may therefore include one or more processing units 50A, such as conventional central processing unit(S) (CPU(s)), and a non-transitory computer-readable memory 50B communicatively coupled to the one or more processing units 50A. The memory 50B may store therein computer-readable instructions 50C. The computer-readable instructions 50C may be executable by the one or more processing units to cause the CAS controller 50 to operate tasks and a surgical workflow such as that of the method 110 described herein. The CAS controller 50 may also guide an operator through the surgical procedure, by providing intraoperative data of position and orientation, and may therefore have the appropriate interfaces such as a mouse, a foot pedal etc. A device with a GUI may be connected to the CAS controller 50 to provide visual guidance through the workflow of the SA system 10, and/or during the method 110.

The tracking apparatus 60 may be used to track the bones of the patient, and the robot arm 20 if present. For example, the tracking apparatus 60 may assist in performing the calibration of the patient bone with respect to the robot arm, for subsequent navigation in a 3-dimensional (X, Y, Z, and corresponding angles) coordinate system.

The camera 70 may be used by the SA system 10 to capture video footage of the surgical procedure. In an embodiment, the camera 70 is a RGB camera. The camera 70 may use scaling markers 70' (FIG. 3) deployed in the surgical field, in the field of view of the camera 70.

The machine-learning module 80 is the learning module of the SA system 10 that receives data from surgical procedures to parametrize/train a machine-learning algorithm (MLA), which may be stored in the non-transitory memory 16 of the server 12, or in any other suitable non-transitory memory such as remote memory on the cloud, for example.

The assistance module 90 is the intervening module of the SA system 10 that provides machine-learned assistance during a surgical procedure based on the parametrized/trained machine-learning algorithm (MLA).

The device(s) 100 displaying the GUI are used by the SA system 10 for example to allow an operator to intervene in the surgical procedure and/or to communicate machine-learned assistance to the operator. For simplicity, the GUI will be referred to as 100, even though the GUI is a display on a device 100.

Though the camera 70 and the GUI 100 are shown as separate components, they may be part of the CAS system. For example, the camera 70 may be the camera of the tracking apparatus 60. The GUI 100 may be that of the CAS system, with the assistance module 90 outputting data through the GUI of the CAS system.

The CAS system may be without the robot arm 20, with the operator performing manual tasks. In such a scenario, the CAS system may only have the CAS controller 50, the tracking apparatus 60 and the GUI 100. In another embodiment, the CAS system is one used without robotic assistance, and assists an operator by way of surgical navigation, i.e., tracking the surgical instrument(s) relative to the bone(s) in orthopedic surgery. The CAS system may also have non-actuated foot support 30 and thigh support 40 to secure the limb. When it operates the robot arm 20, the CAS system may drive the robot arm 20 autonomously, and/or as an assistive or collaborative tool for an operator (e.g., surgeon).

Still referring to FIG. 1, a schematic example of the robot arm 20 is provided. The robot arm 20 may stand from a base 21, for instance in a fixed relation relative to the operating-room (OR) table supporting the patient. The relative positioning of the robot arm 20 relative to the patient is a determinative factor in the precision of the surgical procedure, whereby the foot support 30 and thigh support 40 may assist in keeping the operated limb fixed in the illustrated 3D coordinate system, used by the method 1. The robot arm 20 has a plurality of joints 22 and links 23, of any appropriate form, to support a tool head 24 that interfaces with the patient. The tool head 24 may be a registration pointer, rod or wand, ranging laser, radiation/light transmitter, laser telemeter, to register the bone(s). Registration may also be known as digitizing, and may be defined as recording coordinates of a point or surface in the coordinate system, also known as a frame of reference.

In FIG. 1, the 3D coordinate system is shown, and is a virtual coordinate system, and registration may be recording x,y,z coordinates of points in the 3D coordinate system, as an example. Depending on the type of procedure, the registration may entail a robotic or manual manipulation of a registration pointer contacting points on the surface of the bone, including cartilage, for the points to be registered (i.e., recorded, digitized). Registration may also be done by ranging, for example using a laser with ranging capability (e.g., measuring a distance). Stated differently, registration described herein may be contactless, namely in the form of a radiation transmitter, for example a light transmitter, such as a laser beam, coupled to a distance sensor. In particular, said identification means can be in the form of a laser telemeter. In an embodiment, the laser is manipulated by a robotic arm. As another embodiment, depth cameras may be used to acquire bone surface data. In an optional embodiment, points of bone surface(s) obtained in the 3D coordinate system may be fitted to an existing bone model, whether native or generic, to obtain a virtual 3D bone model that includes some points registered intraoperatively, by contact or by optical ranging. The fitting may be as described in U.S. patent application Ser. No. 16/561,551, incorporated herein by reference.

The arm 20 is shown being a serial mechanism, arranged for the tool head 24 to be displaceable in a desired number of degrees of freedom (DOF). For example, the robot arm 20 controls 6-DOF movements of the tool head 24, i.e., X, Y, Z in the coordinate system, and pitch, roll and yaw. Fewer or additional DOFs may be present to suit each particular type of surgery for example. For simplicity, only a generic illustration of the joints 22 and links 23 is provided, but more joints of different types may be present to move the tool head 24 in the manner described above. The joints 22 are powered for the robot arm 20 to move as controlled by the controller 50 in the six DOFs. Therefore, the powering of the joints 22 is such that the tool head 24 of the robot arm 20 may execute precise movements, such as moving along a single direction in one translation DOF, or being restricted to moving along a plane, among possibilities. Such robot arms 20 are known, for instance as described in U.S. patent application Ser. No. 11/610,728, incorporated herein by reference.

In order to preserve the fixed relation between the leg and the coordinate system, and to perform controlled movements of the leg as described hereinafter, a generic embodiment is shown in FIG. 1. The foot support 30 may be displaceable relative to the OR table, in order to move the leg in flexion/extension (e.g., to a fully extended position and to a flexed knee position), with some controlled lateral movements being added to the flexion/extension. Accordingly, the foot support 30 is shown as having a robotized mechanism by which it is connected to the OR table, with sufficient DOFs to replicate the flexion/extension of the lower leg. Alternatively, the foot support 30 could be supported by a passive mechanism, with the robot arm 20 connecting to the foot support 30 to actuate its displacements in a controlled manner in the coordinate system. The mechanism of the foot support 30 may have a slider 31, moving along the OR table in the X-axis direction. Joints 32 and links 33 may also be part of the mechanism of the foot support 30, to support a foot interface 34 receiving the patient's foot. Moreover, while the leg is shown, the SA system 10 could be used to perform orthopedic surgery on other body parts (e.g. shoulder).

The thigh support 40 may also be robotized, static or adjustable passively. In the latter case, the thigh support 40 may be displaceable relative to the OR table, in order to be better positioned as a function of the patient's location on the table. Accordingly, the thigh support 40 is shown as including a passive mechanism, with various lockable joints to lock the thigh support 40 in a desired position and orientation. The mechanism of the thigh support 40 may have a slider 41, moving along the OR table in the X-axis direction. Joints 42 and links 43 may also be part of the mechanism of the thigh support 40, to support a thigh bracket 44. A strap 45 can immobilize the thigh/femur in the thigh support 40. The thigh support 40 may not be necessary in some instances. However, in the embodiment in which the range of motion is analyzed, the fixation of the femur via the thigh support 40 may assist in isolating joint movements.

The computer-readable instructions 50C of the CAS controller 50, when the CAS controller 50 is used as a robotized surgery controller 50, include instructions which, when executed by the processor(s) 50A, cause the CAS controller 50 to control movement of the robot arm 20, and of the leg support (foot support 30 and thigh support 40), if applicable. To this end, the CAS controller 50 may include additional control hardware, such as conventional control hardware, selected to perform the control of each particular embodiment of the robot arm 20. The CAS controller 50 also provides computer-assisted surgery guidance to an operator via the GUI, whether in the form of a navigation data, model assessment, etc in pre-operatively planning or during the surgical procedure. For instance, the navigation data may be in the form of a surgical workflow, by which the CAS controller 50 suggests a sequence of steps to be executed by the operator. To this end, the system 10 may comprise additional types of interfaces for the information to be provided to the operator, in addition to the GUI 100.

In other embodiments the display(s) 100/GUI may instead be one or more other types of devices providing communications with the operator. The other types of possible communication devices/interfaces may be wireless portable devices (e.g., phones, tablets), audio guidance devices, LED displays, among many possibilities. If a robot arm 20 is present, the controller 50 may then drive the robot arm 20 in performing the surgical procedure based on planning that may be achieved pre-operatively. The controller 50 may do an intra-operative bone model assessment to update the bone model and fit it with accuracy to the patient's bone, and hence enable corrective plan cuts to be made, or guide the selection of implants. The intra-operative bone model assessment may be as an example as described in U.S. patent application Ser. No. 16/561,551, incorporated herein by reference. The controller 50 may also generate a post-operative bone model. To this end, the computer-readable instructions 50C of the CAS controller 50 may therefore include various modules, in the form of algorithms, code, non-transient executable instructions, etc, and the CAS controller 50 may include suitable hardware, which may be required in order to operate the system 10 in the manner described herein.

The use of the tracking apparatus 60 may provide tracking data to perform the bone model updating and subsequent surgical navigation. For example, the tracking apparatus 60 may assist in performing the calibration of the patient's bone with respect to the 3D coordinate system, for subsequent navigation in the 3D coordinate system. According to an embodiment, the tracking apparatus 60 comprises a camera that optically sees and recognizes retro-reflective references 61A, 61B, and 61C, so as to track the tools and limbs for example in six DOFs, namely in position and orientation. The camera of the tracking apparatus 60 may have two or more points of view, to determined the position and orientation of the references 61A, 61B, 61C, by triangulation. This is an option among others, as depth cameras without such references 61 may also be used (e.g., infrared projector with photodetectors). In an embodiment featuring the robot arm 20, the reference 61A is on the tool head 24 of the robot arm 20 such that its tracking allows the controller 50 to calculate the position and/or orientation of the tool head 24 and tool 26A thereon. The references 61 have spheres or patterns of retro-reflective material thereon, arranged in a known geometric arrangement (e.g., scalene triangle). The CAS controller 50 and/or the tracking apparatus 60 recognize the geometric arrangements, such that the position and orientation of the references 61 is trackable. Other tracking modalities may be used as an alternative to the retro-reflective material, include active tracking devices with transmitters and receivers, inertial sensors, etc.

References 61B and 61C may be fixed to the patient-specific devices, known as PSI. For clarity, reference to patient specific/PSI in the present application pertains to the creation of devices that have negative corresponding contour surfaces, i.e., a surface that is the negative opposite of a patient bone/cartilage surface, such that the patient specific surface conforms to the patient bone/cartilage surface, by complementary confirming unique engagement contact. PSI devices may be generated using fabrication techniques such as 3D printing (additive manufacturing), NC machining, laser sintering, fused deposition modelling, stereolithography, laminated object, electron beam melting product, a contour milling product, and computer numeric control product etc, as examples among others. The negative corresponding contour surfaces may be obtained via preoperative imaging (e.g., X-ray, MRI, etc).

In an embodiment without the robot arm 20, references such as reference 61A are on the navigated tools (including a registration tool) such that their tracking allows the controller 50 to calculate the position and/or orientation of the tools and register points. Likewise, references 61B and 61C may be interfaced to the patient bones, such as the femur prior to resection for reference 61B and the femur after resection for reference 61C. Therefore, the controller 50 continuously updates the position and/or orientation of the robot arm 20 and/or tools 26 and patient bones in the 3D coordinate system using the data from the tracking apparatus 60. As an alternative to optical tracking, the tracking apparatus 60 may consist of inertial sensors (e.g., accelerometers, gyroscopes, etc) that produce tracking data to be used by the controller 50 to continuously update the position and/or orientation of the robot arm 20. Other types of tracking technology may also be used, including using the internal control system of the robot arm 20 (e.g., encoders) to determine the position and orientation of the tools 26.

In FIG. 1, the SA system 10 is shown as having the machine-learning (ML) module 80 and the assistance module 90. The ML module 80 performs data acquisition for subsequent training of the MLA.

The data acquisition may take various forms, examples of which are provided below. According to an embodiment, the machine-learning module 80 receives video footage or images from surgical procedures. The footage and/or images may be in the form of an image feed and/or video feed from different types of cameras. For example, the images and/or video feed may be obtained from the camera(s) of tracking apparatus 60, and/or from a dedicated camera(s) 70. Indeed, FIG. 1 shows the camera 70 as being a stand-alone dedicated camera related to the SA system 10 but the data acquisition may be performed using a video feed from other cameras and/or sources such as one or more databases, including one or more databases stored in the memory 50B and/or one or more cloud-based databases having image content and/or video library content, etc. In an embodiment, the camera 70 may be one or more RGB camera(s) and/or depth stereoscopic camera(s) and/or infrared camera(s), and the like. The resolution of the video feed used for machine learning may also vary. In an embodiment, the dedicated camera 70 has a lesser resolution than the camera of the tracking apparatus 60, as the dedicated camera 70 producing the video feed may include off-the-shelf cameras, and mobile device cameras as well.

Data acquisition by the ML module 80 may also include receiving data from the CAS controller 50, or robotized surgery controller 50 in the case of robotized surgery. In some instances, an operator performs surgery with a CAS system but without robotized assistance. In such a case, the data acquisition may include data from the CAS system. Examples thereof are shown in FIGS. 4A-4E, in which the images show the point of view of a dedicated camera 70, along with a screen view of a GUI 100, the screen view being an output for example of the CAS controller 50 during surgical flow. The ML module 80 may supplement image capture from the dedicated camera 70 with an identification of the bone, patient, etc, namely non-confidential data from the CAS controller 50. The data acquired by the ML module 80 may include patient data such as age, gender, race, ethnicity, genetics, height, weight, body mass index, congenital conditions, pathologies, medical history, etc. The data acquired by the ML module 80 may also include surgical flow information from the procedure operated by the CAS controller 50. This may include an identification of tools used, bones being altered, navigation data (e.g., position and/or orientation of tools relative to the bones in a referential system) the parameters of alteration (depth, orientation, navigation data), navigation of robot arm 20 if present. In an embodiment, the data from the CAS controller 50 is synchronized with the video footage. The ML module 80 may also perform a synchronization of video data with control data from the CAS controller 50.

In some instances, an assessment of the surgery is done post-operatively. The ML module 80 may access this information as part of data acquisition as well. The assessment of surgery may take various forms, including quantitative data. In the case of orthopedic surgery, the quantitative data may be distance or length data, such as limb length discrepancy, cut depth. The quantitative data may be orientation data, such as varus/valgus, offset, tilt, etc. The quantitative data may be volumetric data, such as volume of bone removed, volume of resection. The assessment may also include qualitative data, with patient feedback including pain level, perceived mobility, patient satisfaction score, etc. The assessment data may be acquired over a rehabilitation period, with post-operative patient follow ups and the use of wearable sensor technologies, for instance over an extended period of time.

Using the data acquisition, the ML module 80 may train a ML algorithm to understand surgical flow as a function of the particular surgeries.

The training of the ML algorithm may be based on training data acquired from multiple prior surgeries, in different locations, from different SA systems 10, and/or involving different surgeons. The training of the ML algorithm in the ML module 80 may include at least 100 surgical procedures, without an upper echelon of review. The machine learning algorithm may be trained with or without supervision by observing surgeries for patients of different age, gender, race, ethnicity, genetics, height, weight, body mass index, congenital conditions, pathologies, medical history, etc, to train the ML algorithm with procedures covering a wide diversity of cases, including standard cases, and deviation cases. Age, gender, race, ethnicity, genetics, height, weight, body mass index, congenital conditions, pathologies, medical history, etc may have an impact on a surgical flow of a procedure, and cause a deviation over standard procedures. As a consequence of the training of the ML algorithm, the learning module 80 may produce and output a parametrized ML algorithm. The ML algorithm may be selected from different supervised machine learning algorithms, such as neural networks, Bayesian networks, support vector machines, instance-based learning, decision trees, random forests, linear classifiers, quadratic classifiers, linear regression, logistic regression, k-nearest neighbor, hidden Markov models, or the like. The ML algorithm may be selected from different unsupervised machine learning algorithms, such as expectation-maximization algorithms, vector quantization, and information bottleneck method.

The ML module 80 may perform image processing off of the surgery imaging, video feed and/or CAS controller data, in order to identify the various tools and bones used, as well as movements and interactions between them. In an embodiment, the image processing is done locally, in edge computing. This includes observing the geometry of tools, the position and orientation of tools relative to the bones, the bone surfaces including their geometries, the different sizes of tools. The output of image processing may be correlated with CAS controller data, such as bone names, tool names and models. The output of image processing may also be associated patient data, including age, gender, race, ethnicity, genetics, height, weight, body mass index, congenital conditions, pathologies, and/or medical history, etc. The image processing may for example be supervised by the involvement of a reviewer.

The image processing may then be used by the ML algorithm to learn the surgical flow, i.e., observing the geometry of tools, the position and orientation of tools relative to the bones, the bones surfaces including their geometries, the different sizes of tools, and the sequences of steps of surgery vis à vis the specific details of patient data. The learning of the surgical flow may include understanding the sequence of steps of any particular surgical procedure. The sequence of steps of the surgical flow may be correlated with CAS controller data, such as bone names, tool names and models. The sequence of steps of the surgical flow may also be associated to patient data, including age, gender, race, ethnicity, genetics, height, weight, body mass index, congenital conditions, pathologies, and/or medical history, etc. If available, the sequence of steps of the surgical flow may be associated with the assessment of the surgery done post-operatively, such as in the form of the quantitative data and/or qualitative data, to train the ML algorithm in evaluating a surgical flow and its numerous parameters as a function of post-operative assessment. There results a trained ML algorithm in the ML module 80. The trained ML algorithm may have the capacity of performing various functions through its training.

In the image processing of video feed, optionally using various forms of data acquisition as mentioned above if available, the ML algorithm may add bookmarks to the video feed. For example, the bookmarks are in the form of metadata or time stamps in an audio or video track of the video feed. The bookmarks may be associated with particular steps of a surgical flow, deviations from standard surgical flow, rare occurrences, specific scenarios, bone and tool pairings, patient data, etc. The bookmarks may be configured for subsequent retrieval if access to the video feed is desired or required, for instance for training purposes. Accordingly, the ML algorithm may contribute to the creation of an atlas of video footage, with the bookmarks enabling the searching and access of desired video excerpts.

Also with image processing of video feed, optionally using various forms of data acquisition as mentioned above, the ML algorithm may also label steps of surgical workflows. The labelling of such steps may include a start time and a finish time for the surgical step, for segments of a surgical procedure, for groupings of steps, for example. Consequently, a duration of any given step may be measured, and this data may be correlated to the type of surgery, to patient data detailed above, for example, to surgeon identity. The duration data may be used for statistical data. The statistical data may consequently be used for video training, for instance to provide exemplary video segments showing more efficient steps. The statistical data may also be used for surgical workflow optimization.

Figure 2:
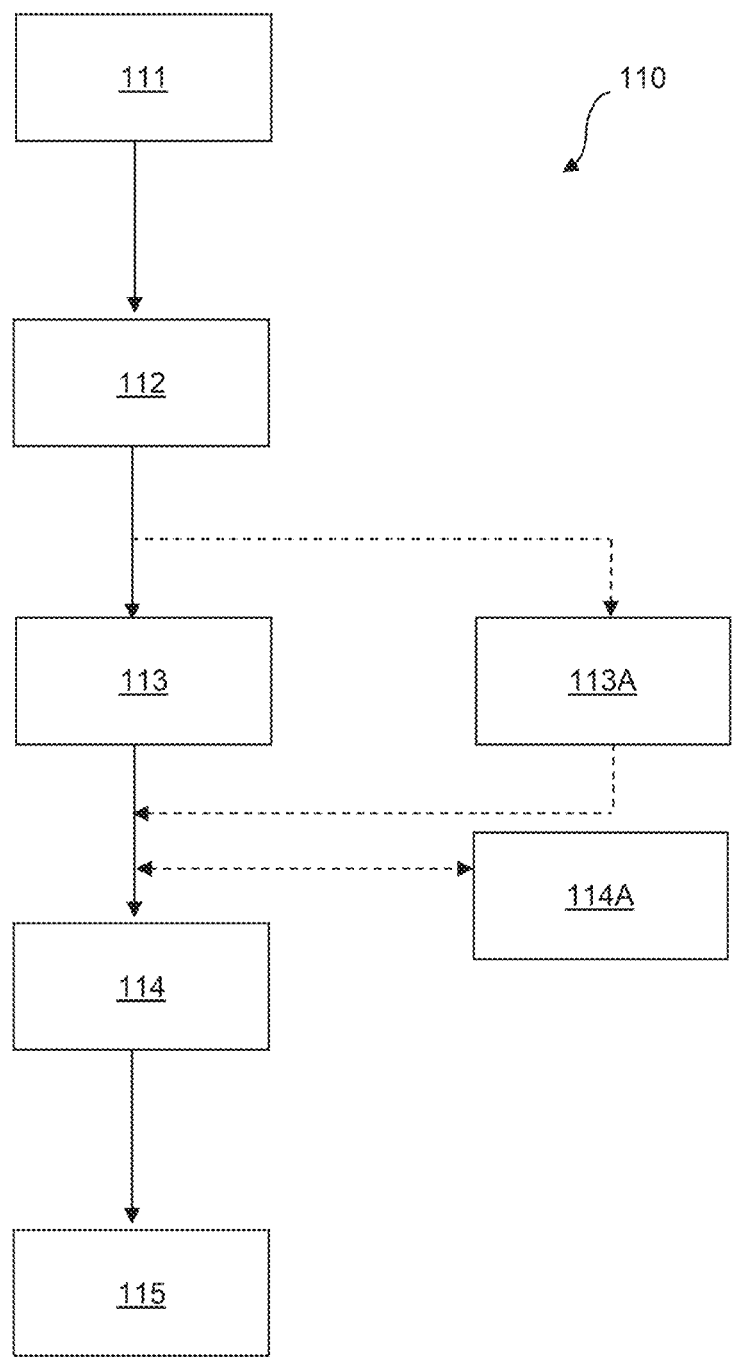
FIG. 2 is a flowchart depicting a surgical flow with deviations caused by the surgery assistance system of FIG. 1.

Referring to FIG. 2, a standard surgical procedure is shown of a method (a.k.a., surgical procedure, surgical flow) 110 having a plurality of steps identified as 111, 112, 113, 114 and 115. The method 110 may be performed with the CAS system described herein, with the assistance of the ML assistance module 90. Steps 111 to 115 represent a surgical flow that occurs mostly intra-operatively. However, some steps of the method 110 may occur pre-operatively, peri-operatively or post-operatively. However, at least some of the steps of the surgical flow 110 occur during surgery. Surgical flow 110 is deemed to represent a standard surgical procedure that applies to a majority of cases for any given surgery, along a standard surgical flow or surgical workflow. Surgery may be knee arthroplasty, hip replacement, hip resurfacing, shoulder arthroplasty, reverse glenoid arthroplasty, among others. In an embodiment, surgical flow 110 implies some form of orthopedic surgery with alterations to a bone. Method 110 may also be the result of the statistical data available through the atlas of surgical procedures, to which the SA system 10 contributes, such as through video capture, labelling and/or bookmarking from the learning module 80. The atlas of surgical procedures may be created by a single SA system 10, multiple systems SA system 10 (e.g., from a single organization or groups), or from an entire population. The SA system 10 may consequently suggest method 110 based on patient data for example, and using the statistical data from the training of the ML algorithm.

Referring to FIGS. 1 and 2, the assistance module 90 has been updated with the parametrized machine learning algorithm. In an embodiment, the assistance module 90 accesses the server 12 in which the parametrized ML algorithm is located, for instance locally in edge computing, but in other embodiments the ML algorithm may be on the cloud for example. During surgery, data acquisition is performed by the assistance module 90. At least some of the forms of data acquisition used by the learning module 80 may be used by the assistance module 90. This includes live video footage from camera 60 and/or 70, communication with the CAS system 50, including the robotized surgery controller 50 of FIG. 1, input from a surgeon, access to post-operative qualitative and/or quantitative assessment data, etc. The assistance module 90 may document the instant surgical procedure, notably by adding bookmarks as set out above, by labelling some of the surgical steps, etc.

Based on output from the parametrized machine learning algorithm, the assistance module 90 may propose a surgical procedure flow, such as method 110, using the available data: patient profile, type of surgery, tool accessibility, nature of procedure. During the surgical procedure, the assistance module 90 may retrieve and offer for display video segments of an upcoming surgical step of the surgical procedure. The retrieving may be done using bookmarks on videos of prior surgical procedures.

Based on output from the parametrized machine learning algorithm, the assistance module 90 may detect a condition or conditions requiring a deviation from the surgical flow 110. A deviation may be defined as being a step that occurs in less than the majority of cases and/or a step or action being outside of a standard surgical flow. This may include exceptional steps based on specific conditions and/or abnormal anatomical features, which may be the result of any of age, gender, race, ethnicity, genetics, height, weight, body mass index, congenital conditions, pathologies, medical history, etc. Assistance module 90 may therefore output a recommendation to deviate from the surgical flow 110. Alternatively, the assistance module 90 may automatically create a deviation in the surgical flow 110, for example to be confirmed by the surgeon. This is shown as step 113a in FIG. 2. Step 113a may be the substitution of the normal work flow step 113 by a deviation step 113a. As also shown in FIG. 2, the recommendation may be in the form of an additional step or steps before pursuing the normal surgical flow 110. This is illustrated as 114a. In yet another embodiment, the recommendation made by the assistance module 90 may be in the form of a reversal of steps of the surgical flow, or a repeat of a step, or a cancellation of a step. The condition or conditions requiring a deviation from the surgical flow 110 may also be based on an efficiency criteria, with the deviation deemed to allow the surgical procedure to be performed more efficiently. The deviation may be based on statistical data from the ML algorithm.

To illustrate the concept of deviation, some non-limitative examples are given. These examples may apply to orthopedic surgery, but the concept of deviation in a surgical flow 110. According to an embodiment, the surgical flow 110 may be planned for use of a cementless implant. At 113, the planned action may be to secure the cementless implant to the bone, using appropriate technique associated with cementless. The assistance module 90, through its data acquisition, may detect bone quality or bone condition. This may be correlated to an age of a patient. Consequently, the assistance module 90 may indicate that the bone condition is inappropriate for cementless implant. The assistance module 90 may then recommend a change to cemented implant as output, as a substitute deviation action 113*a*. According to another embodiment, in the context of knee surgery, the planned action at 113*a* may be the resurfacing of a medial compartment of the tibial plateau, in a medial partial knee surgery. The assistance module 90, through its data acquisition, may detect that the lateral compartment also appears to have damage. The assistance module 90 may then recommend a change to total knee arthroplasty, as 113A, instead of the planned action 113. As yet another exemplary embodiment, a planned action 113 may pertain to a cruciate retaining design. The assistance module 90, through its data acquisition, may detect damage to the posterior cruciate ligament. The assistance module 90 may consequently recommend a change to a posterior stabilizing design, in deviation action 113*a*. In another exemplary embodiment, for a patient with severe valgus deformity, the assistance module 90, through its data acquisition, may assess the severity of the deformity. Before the planned resection/implanting action of 114, the assistance module 90 may recommend that soft tissue releases and/or an osteotomy be performed as action 114A, before the planned resection/implanting action of 114. As another embodiment, the planned surgical flow in knee replacement may not have taken into consideration patellar conditions. The assistance module 90, through its data acquisition, may recognize patellar subluxation and/or patellar maltracking. An additional action at 114A of resurfacing of the patella may be recommended by the assistance module 90.

Figure 3:
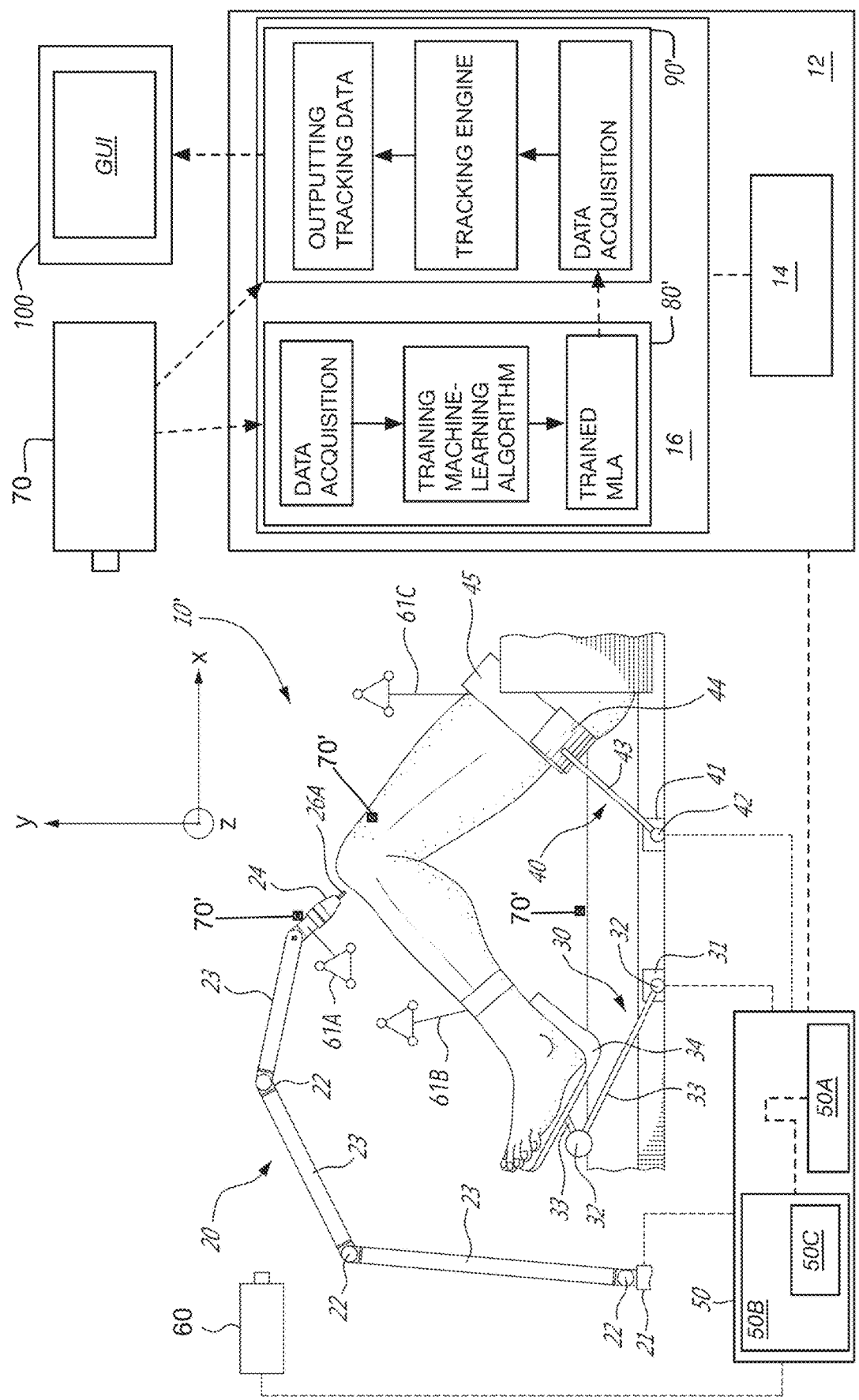
FIG. 3 is a schematic view of a surgery assistance system in accordance with a second embodiment of the present disclosure.

Referring to FIG. 3, another embodiment of the SA system is shown at 10'. The SA system 10' has a similar configuration of software and hardware as in the embodiment of FIG. 1, whereby like reference components will bear like reference numerals. The SA system 10' is shown relative to a patient's knee joint in supine decubitus, but only as an example. The SA system 10' could be used for other body parts, including non-exhaustively hip joint, spine, and shoulder bones.

The SA system 10' of FIG. 3 may or may not be robotized. The SA system 10' may operate in parallel with a computer-assisted surgery (CAS) system that may optionally be a robotized surgery system. The CAS system may include a robot arm 20, a foot support 30, a thigh support 40, a CAS controller 50 which may be a robotized surgery controller if a robot arm 20 is used, and/or a tracking apparatus 60. The CAS system may be used independently of machine-learning assistance, but over time, machine-learning assistance may assist and operate the tracking as an alternative to the tracking apparatus 60, in the manner described below. The SA system 10 may include a camera 70, a machine-learning module 80', and an assistance module 90' in the form of computer-readable instructions in the memory 16. One or more devices 100, such as monitors, tablets, phones, and the like, may be operatively connected to the server 12 and may display a graphical-user interface (GUI):

The robot arm 20 is optional and is operatively connected to and is the working end of the SA system 10 in an embodiment featuring robotics, and is used to perform bone alterations as planned by an operator and/or the CAS controller 50 and as controlled by the CAS controller 50.

The foot support 30 is optional and supports the foot and lower leg of the patient, in such a way that it is only selectively movable. The foot support 30 is robotized in that its movements can be controlled by the CAS controller 50.

The thigh support 40 is optional and supports the thigh and upper leg of the patient, again in such a way that it is only selectively or optionally movable. The thigh support 40 may optionally be robotized in that its movements can be controlled by the CAS controller 50.

The CAS controller 50 operates the surgical workflow. The CAS controller 50 may also control the robot arm 20, the foot support 30, and/or the thigh support 40. The CAS controller 50 may therefore include one or more processing units 50A, such as conventional central processing unit(S) (CPU(s)), and a non-transitory computer-readable memory 50B communicatively coupled to the one or more processing units 50A. The memory 50B may store therein computer-readable instructions 50C. The computer-readable instructions 50C may be executable by the one or more processing units to cause the CAS controller 50 to operate tasks and a surgical workflow. The CAS controller 50 may also guide an operator through the surgical procedure, by providing intraoperative data of position and orientation, and may therefore have the appropriate interfaces such as a mouse, a foot pedal etc. A device with a GUI may be connected to the CAS controller 50 to provide visual guidance through the workflow of the SA system 10.

The tracking apparatus 60 may be used to track the bones of the patient, and the robot arm 20 if present. For example, the tracking apparatus 60 may assist in performing the calibration of the patient bone with respect to the robot arm, for subsequent navigation in a 3-dimensional (X, Y, Z, and corresponding angles) coordinate system. After the training of the ML module 80', the tracking apparatus 60 may no longer be required.

The camera 70 may be used by the SA system 10' to capture video footage of the surgical procedure. In an embodiment, the camera 70 is a RGB camera.

The machine-learning module 80' is the learning module of the SA system 10' that receives data from surgical procedures to parametrize/train a machine-learning algorithm (MLA), which may be stored in the non-transitory memory 16 of the server 12, or in any other suitable non-transitory memory such as remote memory on the cloud, for example.

The assistance module 90' is the intervening module of the SA system 10' that provides machine-learned assistance during a surgical procedure based on the parametrized/trained machine-learning algorithm (MLA), to replace the tracking apparatus 60.

The device(s) 100 displaying the GUI are used by the SA system 10' for example to allow an operator to intervene in the surgical procedure and/or to communicate machine-learned assistance to the operator. For simplicity, the GUI will be referred to as 100, even though the GUI is a display on a device 100.

Though the camera 70 and the GUI 100 are shown as separate components, they may be part of the CAS system. For example, the camera 70 may be the camera of the tracking apparatus 60. In similar fashion to the embodiment of FIG. 1, the use of the tracking apparatus 60 may provide tracking data to perform the bone model updating and subsequent surgical navigation, until the assistance module 90' can perform and output the tracking. According to an embodiment, the tracking apparatus 60 comprises a camera that optically sees and recognizes the retro-reflective references 61A, 61B, and 61C (concurrently, 61), so as to track the tools and limbs in for example six DOFs, namely in position and orientation, the camera 60 having for example two points of view and operating via triangulation. The SA system 10' is shown as having the machine-learning (ML) module 80' and the assistance module 90', that are used to perform the tracking without retro-reflective references 61, after training. Moreover, the SA system 10' may optionally perform the tracking without the camera of the tracking apparatus 60, using instead a lower resolution camera, shown as 70. In an embodiment the camera 70 is mounted onto the tracking apparatus 60 to have a similar perspective as that of the tracking apparatus 60. The ML module 80' performs data acquisition for subsequent training of the MLA.

The data acquisition may take various forms, examples of which are provided below. According to an embodiment, the machine-learning module 80' receives video footage or images from surgical procedures. The footage and/or images may be in the form of an image feed and/or video feed from the tracking apparatus 60 and/or camera(s) 70. FIG. 3 shows the camera 70 as being a stand-alone dedicated camera related to the SA system 10' but the data acquisition may be performed using a video feed from other cameras and/or sources such as one or more databases, including one or more databases stored in the memory 50B and/or one or more cloud-based databases having image content and/or video library content, etc. In an embodiment, the camera 70 may be one or more RGB camera(s) and/or depth stereoscopic camera(s) and/or infrared camera(s), and the like. The resolution of the video feed used for machine learning may also vary. In an embodiment, the dedicated camera 70 has a lesser resolution than the camera of the tracking apparatus 60, as the dedicated camera 70 producing the video feed may include off-the-shelf cameras, and mobile device cameras as well.

Data acquisition by the ML module 80' may also include receiving data from the CAS controller 50, or robotized surgery controller 50 in the case of robotized surgery. In some instances, an operator performs surgery with a CAS system but without robotized assistance. In such a case, the data acquisition may include tracking data from the CAS system, as produced and output by the tracking apparatus 60. The tracking data includes the position and orientation of the objects (e.g., bones, tools, instruments) in the 3D coordinate system. This may include an identification of tools used, bones being altered, navigation data, the parameters of alteration (depth, orientation, navigation data), navigation of robot arm 20 if present. The data acquired by the ML module 80' may also include surgical flow information from the procedure operated by the CAS controller 50. The data acquired by the ML module 80' may include patient data such as age, gender, race, ethnicity, genetics, height, weight, body mass index, congenital conditions, pathologies, medical history, etc. In an embodiment, the data from the CAS controller 50 is synchronized with the video footage. The ML module 80' may also perform a synchronization of video data with control data from the CAS controller 50.

In some instances, an assessment of the surgery is done post-operatively. The ML module 80 may access this information as part of data acquisition as well. The assessment of surgery may take various forms, including quantitative data. In the case of orthopedic surgery, the quantitative data may be distance or length data, such as limb length discrepancy, cut depth. The quantitative data may be orientation data, such as varus/valgus, offset, tilt, etc. The quantitative data may be volumetric data, such as volume of bone removed, volume of resection.

Using the data acquisition, the ML module 80' may train a ML algorithm to understand surgical flow, and track objects as part of the surgical flow, using the video feed from the tracking apparatus 60 and/or the camera(s) 70.

The ML module 80' may perform image processing off of the surgery imaging, video feed and/or CAS controller data, in order to identify the various tools and bones used, as well as movements and interactions between them. This includes observing the geometry of tools, the position and orientation of tools relative to the bones, the bones surfaces including their geometries, the different sizes of tools. The output of image processing may be correlated with CAS controller data, such as bone names, tool names and models. The output of image processing may also be associated patient data, including age, gender, race, ethnicity, genetics, height, weight, body mass index, congenital conditions, pathologies, and/or medical history, etc.

In an embodiment, the ML module 80' may use additional sources of information, to perform tracking calculations in a parallel and redundant manner over the tracking performed by the tracking apparatus 60. The parallel redundant tracking in the ML phase may be performed using scaling markers 70'. The scaling markers 70' may be permanently installed in the field of view in the OR to assist with depth perception and orientation in the video feed. The scaling markers 70' may be flat patterned tags, for example, but other scaling markers 70' could be used, including polygonal markers, etc. As another example of parallel redundant tracking, the ML module 80' may obtain robot arm 20 tracking data, from the CAS controller 50. The robot arm 20 has encoders and like sensors to control its operation. Accordingly, using the data coming from the controlling of the robot arm 20, the ML module 80' may perform this parallel redundant tracking over the tracking performed by the tracking apparatus 60.

The training of the ML algorithm in the ML module 80' may include at least 100 surgical procedures, without an upper echelon of review. The machine learning algorithm may be trained with or without supervision by observing surgeries and performing for instance tracking parallel to that performed using the tracking apparatus 60, with a video feed from the tracking apparatus 60 and/or the camera 70 if present. According to an embodiment, the ML module 80' leans the surgical flow, and steps performed by an operator or by the robot arm 20 as part of the surgical flow. For example, the ML module 80' may learn how certain anatomical features look from its point of view (e.g., lateral epicondyle, anterior cortex, tibial tuberosity etc.) in relation to the 3D bone model it observes in the CAS controller 50. With reference to FIGS. 4A to 4E, there is illustrated the concurrent footage from the dedicated camera 70 with the output from the CAS controller 50 on the GUI 100. The ML module 80' may use the information from the CAS controller 50 to associate the footage, and image processing thereof, with the names, models, of the surgical flow. In an example, the ML module 80' learns how to recognize cut planes on the video feed relative to the bone—the camera 70 produces video feed as the saw intersects the bone, with the saw or other tool is acting as a planar registration pointer of sorts for the resection. In such an embodiment, the camera 70 can use scaling markers 70' or encoder output from the robot arm 20 to assist with depth perception and orientation in the video feed.

Figure 4A:
FIG. 4A is an image of concurrent image tracking and controller surgical flow for obtaining landmark points on a tibial plateau, by the surgery assistance system of FIG. 1 or of FIG. 3.
Figure 4B:
FIG. 4B is an image of concurrent image tracking and controller surgical flow for obtaining landmark points on a distal femur, by the surgery assistance system of FIG. 1 or of FIG. 3.
Figure 4C:
FIG. 4C is an image of concurrent image tracking and controller surgical flow for a cut guide on a tibial plateau, by the surgery assistance system of FIG. 1 or of FIG. 3.
Figure 4D:
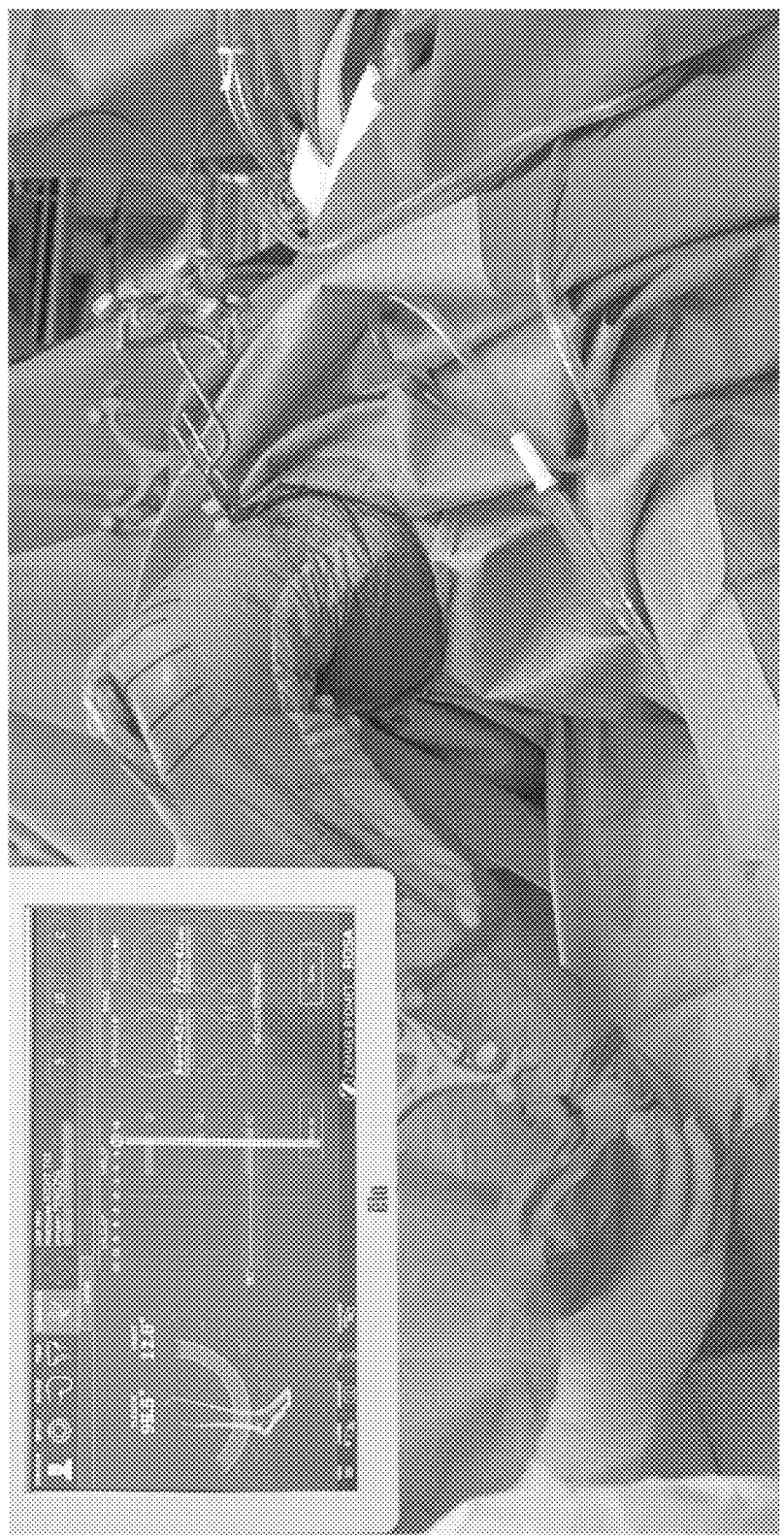
FIG. 4D is an image of concurrent image tracking and controller surgical flow for a knee range of motion and varus/valgus assessment, by the surgery assistance system of FIG. 1 or of FIG. 3.
Figure 4E:
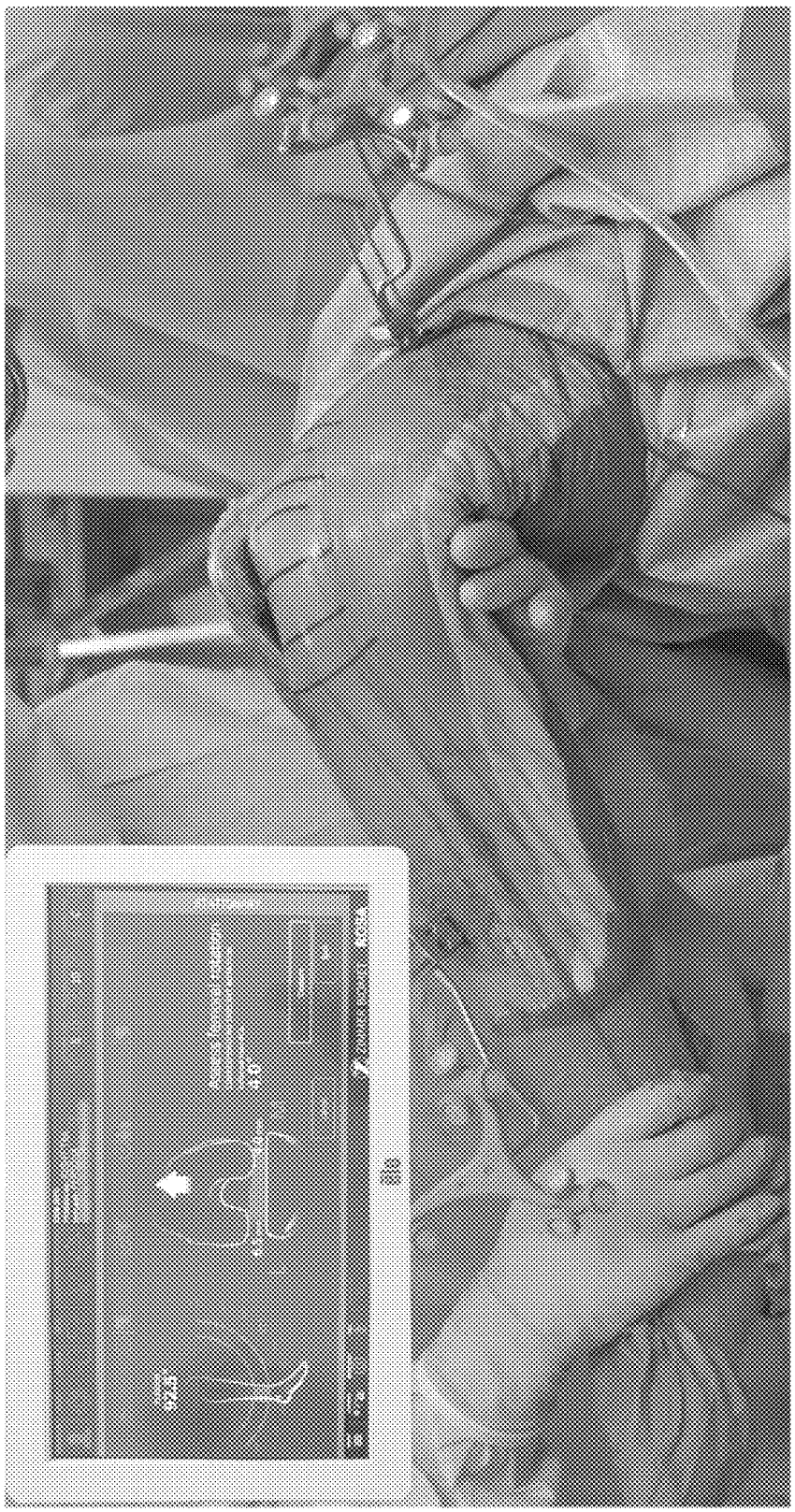
FIG. 4E is an image of concurrent image tracking and controller surgical flow for femoral rotation and soft tissue balancing, by the surgery assistance system of FIG. 1 or of FIG. 3.

FIG. 4A is an image of concurrent image tracking and controller surgical flow for obtaining landmark points on a tibial plateau, by the SA system 10', in a digiziting step for the registration of bone landmarks in the coordinate system. FIG. 4B is an image of concurrent image tracking and controller surgical flow for obtaining landmark points on a distal femur, by the SA system 10', again in a digiziting step for the registration of landmarks in the coordinate system. FIG. 4C is an image of concurrent image tracking and controller surgical flow for a cut guide on a tibial plateau, by the SA system 10', by which cut values are displayed while resection occurs. FIG. 4D is an image of concurrent image tracking and controller surgical flow for a knee range of motion and varus/valgus assessment, by the SA system 10'. FIG. 4E is an image of concurrent image tracking and controller surgical flow for femoral rotation and soft tissue balancing, by the SA system 10'. While these FIGS. 4A-4E are explained with reference to FIG. 3, they may be used by the SA system 10 of FIG. 1, and may constitute actions in the method 110.

As a consequence of the training of the ML algorithm, the learning module 80' may produce and output a parametrized ML algorithm. The ML algorithm may be selected from different supervised machine learning algorithms, such as neural networks, Bayesian networks, support vector machines, instance-based learning, decision trees, random forests, linear classifiers, quadratic classifiers, linear regression, logistic regression, k-nearest neighbor, hidden Markov models, or the like. The ML algorithm may be selected from different unsupervised machine learning algorithms, such as expectation-maximization algorithms, vector quantization, and information bottleneck method.

Referring to FIG. 3, the assistance module 90' is updated with the parametrized machine learning algorithm. In an embodiment, the assistance module 90' accesses the server 12 in which the parametrized ML algorithm is located, but in other embodiments the ML algorithm may be on the cloud for example. During surgery, data acquisition is performed by the assistance module 90'. At least some of the forms of data acquisition used by the learning module 80' may be used by the assistance module 90'. This includes live video footage from camera 60 and/or 70, but without data from the references 61, communication with the CAS system 50, including the robotized surgery controller 50 of FIG. 3, input from a surgeon, etc. This may include data from the robot arm encoders (if present) and the presence of scaling markers 70' in the field of view of the camera 70.

Based on output from the parametrized machine learning algorithm, the assistance module 90' has a tracking engine to determine the relative position and orientation of objects in the 3D reference system, from the video feed. The assistance module 90' may output tracking data in real time. Thus, after a given number of cases in a particular environment, the tracking apparatus 60 and references 61 may no longer be required, with the video feed from the camera 70 sufficing for the assistance module 90' to track the objects during surgery. With complete training of the ML module 80', the SA system 10' may consequently rely on intra-operative data to perform surgery if X-ray of CT imaging is not available. In order to address obstruction constraints, i.e., such as items that do not have a direct line of sight with camera 70 (e.g., posterior condyles), the geometry of such items may be inferred from the known geometry of tools that contacts such items. Moreover, numerous of the camera 70 may be used in a network setting, with the assistance module 90' using the multiple feeds of the numerous cameras 70 to perform a continuous tracking. Accordingly, the assistance module 90' of the SA system 10' may allow navigated surgeries to take place without the tracking apparatus 60, the SA system 10' using lower resolution cameras and/or no references 61. Notably, due to the greater availability of such cameras, it may be possible to use numerous cameras 70 and obtain greater coverage of the surgical site.

The invention claimed is:

1. A surgical assistance system for assisting in a surgical procedure, comprising:
    a processing unit;
    a machine learning module; and
    a non-transitory computer-readable memory communicatively coupled to the processing unit and comprising computer-readable program instructions executable by the processing unit for:
    obtaining video footage of prior surgical procedures;
    using at least the video footage of prior surgical procedures, training the machine learning module to recognize a standard surgical flow that applies to a majority of the prior surgical procedures and to determine conditions requiring a deviation from the standard surgical flow, the deviation being defined as a required step or action being outside of the standard surgical flow;
    obtaining a video feed of the surgical procedure and monitoring the surgical procedure from the video feed;
    detecting, from an image processing of the video feed and with the machine learning module, one of the conditions requiring a deviation from the surgical procedure; and
    outputting a recommendation of deviation by intra-operatively providing the recommendation to an operator of the surgical procedure.

2. The surgical assistance system of claim 1, wherein the machine learning module is trained by performing image processing of the video feed of prior surgical procedures.

3. The surgical assistance system of claim 1, wherein the machine learning module is trained by receiving control data associated with the video feed from computer-assisted surgery controllers of the prior surgical procedures.

4. The surgical assistance system of claim 1, wherein the machine learning module is trained by receiving patient data associated with the video feed, the patient data including one or more of age, gender, race, ethnicity, genetics, height, weight, body mass index, congenital conditions, pathologies, medical history.

5. The surgical assistance system of claim 1, wherein the machine learning module is trained by receiving tool data associated with the video feed.

6. The surgical assistance system of claim 1, wherein the machine learning module is trained by receiving post-operative assessment data associated with the prior surgical procedures.

7. The surgical assistance system of claim 6, wherein receiving post-operative assessment data includes receiving quantitative post-operative assessment data.

8. The surgical assistance system of claim 6, wherein receiving post-operative assessment data includes receiving qualitative post-operative assessment data.

9. The surgical assistance system of claim 1, wherein obtaining a video feed of a surgical procedure includes receiving a RGB camera video feed.

10. The surgical assistance system of claim 1, wherein obtaining a video feed of a surgical procedure and monitoring the surgical procedure from the video feed includes receiving the video feed from a tracking apparatus used in the surgical flow.

11. The surgical assistance system of claim 1, further including receiving control data associated with the video feed of the surgical procedure from a computer-assisted surgery controller of the surgical procedure.

12. The surgical assistance system of claim 1, further including receiving patient data associated with the video feed of the surgical procedure, the patient data including one or more of age, gender, race, ethnicity, genetics, height, weight, body mass index, congenital conditions, pathologies, medical history.

13. The surgical assistance system of claim 1, wherein outputting a recommendation of deviation includes outputting a recommendation of substitution of at least one step from the standard surgical flow.

14. The surgical assistance system of claim 1, wherein outputting a recommendation of deviation includes outputting a recommendation of at least one additional step before pursuing the standard surgical flow.

15. The surgical assistance system of claim 1, wherein outputting a recommendation of deviation includes outputting a recommendation of cancelling at least one step before pursuing the standard surgical flow.

16. The surgical assistance system of claim 1, wherein outputting a recommendation of deviation includes outputting a recommendation of repeating at least one step before pursuing the standard surgical flow.

17. The surgical assistance system of claim 1, wherein monitoring the surgical procedure from the video feed includes inserting at least one bookmark in the video feed.

18. The surgical assistance system of claim 1, wherein monitoring the surgical procedure from the video feed includes labelling at least one step of the surgical procedure in the video feed.

\* \* \* \* \*